United States Patent
Neubauer et al.

(10) Patent No.: US 9,033,997 B2
(45) Date of Patent: May 19, 2015

(54) EXPRESS-REGISTERING REGIONS OF THE BODY

(75) Inventors: Timo Neubauer, Grasbrunn-Neukeferloh (DE); Frank Uhing, München (DE)

(73) Assignee: Brainlab AG, Feldkirchen (DE)

( * ) Notice: Subject to any disclaimer, the term of this patent is extended or adjusted under 35 U.S.C. 154(b) by 1318 days.

(21) Appl. No.: 12/793,002

(22) Filed: Jun. 3, 2010

(65) Prior Publication Data

US 2010/0307516 A1  Dec. 9, 2010

Related U.S. Application Data

(60) Provisional application No. 61/233,520, filed on Aug. 13, 2009.

(30) Foreign Application Priority Data

Jun. 3, 2009 (EP) .................................. 09 161 829

(51) Int. Cl.
*A61B 19/00* (2006.01)
*A61B 5/00* (2006.01)
*A61B 5/103* (2006.01)

(52) U.S. Cl.
CPC ............... *A61B 5/4504* (2013.01); *A61B 5/103* (2013.01); *A61B 19/5244* (2013.01); *A61B 2019/505* (2013.01); *A61B 2019/5255* (2013.01); *A61B 2019/5268* (2013.01); *A61B 5/6878* (2013.01)

(58) Field of Classification Search
USPC ............... 606/130, 1; 600/407, 411, 414, 417
See application file for complete search history.

(56) References Cited

U.S. PATENT DOCUMENTS

2008/0228188 A1  9/2008  Birbeck et al.

FOREIGN PATENT DOCUMENTS

| DE | 10 2006 020 399 | 10/2007 | |
|----|----|----|----|
| EP | 2 044 884 | 4/2009 | |
| WO | WO 2006100458 A2 * | 9/2006 | ............ A61B 17/17 |
| WO | 2006/106335 | 10/2006 | |
| WO | 2007067150 | 6/2007 | |
| WO | 2007/117695 | 10/2007 | |

* cited by examiner

*Primary Examiner* — Thomas McEvoy
(74) *Attorney, Agent, or Firm* — Tucker Ellis LLP

(57) ABSTRACT

The present invention relates to a method for determining the region of the body in which an anatomical part of the body is situated, said method including the following steps:
anatomical point data is provided which includes information concerning a spatial pattern of positions of patient landmarks of a part of a patient's body which corresponds to the anatomical part of the body;
landmark data is provided which includes information concerning a spatial pattern of positions of model landmarks of a model of the anatomical part of a patient's body;
wherein, assuming that
the patient landmarks represent the same landmarks as the model landmarks,
the region of the body in which the part of the patient's body is situated is determined on the basis of the landmark data and the anatomical point data.

12 Claims, 4 Drawing Sheets

EXPRESS-REGISTERING REGIONS OF THE BODY

RELATED APPLICATION DATA

This application claims the priority of U.S. Provisional Application No. 61/233,520, filed on Aug. 13, 2009, which is hereby incorporated in its entirety by reference.

FIELD OF THE INVENTION

The present invention relates to a method for determining the region of the body, in particular a right-hand or left-hand side of the body, in and/or on which an anatomical part of the body—for example, a lower leg bone (in particular, a tibia and/or fibula)—is situated which is in particular formed to be substantially symmetrical to a part of the body which lies on the other side and/or in another region of the body.

BACKGROUND OF THE INVENTION

In surgical navigation methods (IGS=image-guided surgery), the surgeon regularly needs to assign parts of the body, which for example are arranged symmetrically on different sides of the body, to the corresponding side. A problem exists here, in that a right lower leg bone and a left lower leg bone can for example exhibit a congruent shape and/or view, depending on the position of the observer and/or the perspective from which the bone is observed. This leads to a problem in assigning the corresponding part of the patient's body to the corresponding parts of the body in the model data set of the patient's body which is stored before the operation. In particular, the part of the patient's body can no longer be clearly incorporated into the model data set.

Within this context, a "part of the patient's body" is understood to mean the actual part of the patient's body. The part of the patient's body is to be distinguished from a virtual model of the part of the body which is encompassed by a model data set of the actual part of the patient's body. A part of the patient's body is also referred to here as an anatomical part of the body. The part of the patient's body has hitherto been assigned to a particular region of the body—for example, a shin bone (tibia) has been assigned to the right leg or left leg of the patient—by the surgeon making a manual input into a data processing device. This can however result in errors, which can for example be based on an incorrect input by the user. Inputting also takes time.

SUMMARY OF THE INVENTION

It is thus an object of the following invention to provide a method for automatically determining the region of the body in which the part of the patient's body is actually situated, in order to simplify assigning the part of the patient's body to the model data set. The intention is in particular to use the method in accordance with the invention to ascertain the side of the body (i.e. the left or right half) on which the part of the patient's body is arranged, i.e. whether it is a right-hand or left-hand part of the body. This is also referred to in the following as "lateral determination". Alternatively or additionally, however, the term "lateral determination" can also include determining the region of the body in which the anatomical part of the body is situated. In this respect, the term "region of the body" can encompass the term "side of the body"; in particular, these terms can be used interchangeably.

This object is solved by the subject of the independent claims. The dependent claims comprise advantageous embodiments of the invention, wherein the features of different embodiments of the invention can be combined with each other.

In order to determine the region of the body in which an anatomical part of the body is situated, the following steps are advantageously performed: anatomical point data is provided which includes information concerning a spatial pattern of positions of patient landmarks of a part of a patient's body which corresponds to the anatomical part of the body. A patient landmark is a landmark, in particular an anatomical landmark, on the body of the patient.

An anatomical landmark is understood to mean a defined characteristic point of an anatomical structure which is always identical or recurs with a high degree of similarity in the same anatomical structure of multiple patients. Typical landmarks are for example the epicondyles of a femoral bone or the tips of the transverse processes and/or dorsal process of a vertebra. Landmarks which are situated on the part of the patient's body are referred to in the following as patient landmarks; landmarks which are defined in a model of the part of the patient's body are referred to as model landmarks. If a method step within the framework of this invention can be or is applied to both patient landmarks and model landmarks, then only "landmarks" are mentioned in the following.

Anatomical landmarks are to be distinguished from artificial landmarks. Artificial landmarks can be defined on anatomical structures which usually are not always identical or do not recur with a high degree of similarity in the same anatomical structure of multiple patients. In particular, artificial landmarks can be defined by attaching a marker device and/or a reference star to the anatomical structure and/or by the relative position of the marker device and/or reference star with respect to the anatomical structure.

The part of the patient's body is in particular a tibia and/or fibula which is to be assigned to the right or left leg of the patient, such that a surgical navigation system automatically identifies whether it is for example a right or left tibia and/or a right or left fibula, without an input by the user being necessary for this purpose. The method in accordance with the invention can however also be applied to other parts of the body, for example a scapula or a humerus.

The anatomical point data is advantageously referenced using a pointer. A pointer is a rod comprising one or more—advantageously, two—markers affixed to it, wherein the pointer can be used to tap individual co-ordinates, in particular spatial co-ordinates (i.e. three-dimensional co-ordinates), on a part of the body within the framework of referencing, wherein a user guides the pointer (in particular, a part of the pointer which has a defined and advantageously fixed position with respect to the at least one marker which is attached to the pointer, for example the tip of the pointer) to the location corresponding to the co-ordinates, such that the location of the pointer can be determined by detecting the marker on the pointer using a surgical navigation system. The relative position between the markers of the pointer and the part of the pointer used to tap co-ordinates (in particular, the tip of the pointer) is in particular known. The surgical navigation system then enables the location (the three-dimensional co-ordinates) to be assigned to a predetermined body structure (in particular, a model data set of the body structure), wherein the assignment can be made automatically and/or by user intervention. Referencing thus allows the anatomical point data to be digitized and enables it to be processed by a digital data processing device.

The position of an object is understood to mean a description of its spatial location (in particular, its location in three-dimensional space), which can be described for example by vectors using Cartesian and/or spherical co-ordinates, and advantageously an alignment of the object. The alignment follows for example from direction information, in particular the direction of a vector from the object to another object. If the position includes direction information, then it is advantageously referred to as a relative position and/or a position relative to an object.

The position of a patient landmark is understood to mean its co-ordinates in a local co-ordinate system (in relation for example to the patient's body) or a global co-ordinate system (in relation for example to a working environment such as the operating theatre). The position of a patient landmark is in particular ascertained as a point defined by the pointer and/or the tip of the pointer during referencing. The anatomical point data which includes information concerning such positions of the patient landmarks is thus provided in accordance with the invention by being recorded by a surgical navigation method during referencing. The patient landmarks can all lie in one plane, but are advantageously referenced in such a way that this is not the case (i.e. advantageously, at least one patient landmark does not lie in a plane with the other patient landmarks). This can simplify lateral determination.

Landmark data is also provided which includes information concerning a spatial pattern of positions of model landmarks of a model of the anatomical part of the patient's body.

Information concerning the position of the patient landmarks and/or the model landmarks relative to the position of at least one reference point on the anatomical part of the body and/or in the model is advantageously known. The reference point can for example be identified by a marker device. The reference point can in particular lie at the point at which a marker device borders the part of the patient's body and/or at which it penetrates the surface of a bone. The reference point can alternatively or additionally lie in a component of a marker device. A plurality of reference points, in particular two or three reference points, can increase the accuracy of the method in accordance with the invention.

The reference point in the part of the patient's body and the reference point in the model are advantageously equivalent to each other, i.e. they in particular have an identical or similar position and/or geometric relationship relative to other particular parts of the body, in particular to the anatomical part of the body being observed in the method in accordance with the invention.

A marker device can be a reference star, a pointer and/or one or more markers. It is the function of a marker to be detected by a marker detection device (for example, a camera or an ultrasound receiver), such that its spatial position (i.e. its spatial location and/or alignment) can be ascertained. Such markers can be active markers. An active marker emits for example electromagnetic radiation and/or waves, wherein said radiation can be in the infrared, visible and/or ultraviolet spectral range. The marker can also however be passive, i.e. can for example reflect electromagnetic radiation from the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A "reference star" refers to a device with a number of markers, advantageously three markers, attached to it, wherein the markers are attached to the reference star such that they are stationary and advantageously detachable, such that a known (and advantageously fixed) position of the markers relative to each other is provided. The position of the markers relative to each other can be individually different for each reference star used within the framework of a surgical navigation method, in order to enable the corresponding reference star to be identified by a surgical navigation system on the basis of the position of the markers relative to each other. It is therefore also then possible for the objects (for example, instruments and/or parts of the body) to which the reference star is attached to be identified and/or distinguished from each other. In a surgical navigation method, the reference star serves to attach a plurality of markers to an object (for example, a bone and/or an anatomical part of the body or a medical instrument) in order to be able to detect the spatial position of the object (i.e. its spatial location and/or alignment). Such a reference star in particular includes a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to. Where it is clear from the context, the term "reference star" can also refer to a reference star together with at least one marker attached to it. Such a system consisting of a reference star and at least one marker can also be referred to as a marker star.

A surgical navigation system and/or navigation system is understood to mean a system which consists of: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) includes a processor (CPU), a working memory, advantageously an indicating facility (for example a visual indicating facility such as a monitor and/or an audio indicating facility such as a loudspeaker) and advantageously a permanent data memory, wherein the data processing device processes navigation data forwarded to it by the receiver and can advantageously output guidance information to a user via the indicating facility. The navigation data can be stored in the permanent data memory and for example compared with data which has been provided in said memory beforehand.

Where data is "provided", this means that it is ready for use by the method in accordance with the invention. The data can achieve this state of being "provided" by for example being captured (for example by analysis apparatus) or by being input (for example via interfaces). The data can also have this state by being stored in a memory (for example a ROM, CD and/or hard disc) and thus ready for use within the framework of the method in accordance with the invention.

The provided data of at least parts of the patient's body (in particular the part of the patient's body being observed in the method in accordance with the invention) can for example be obtained using medical imaging methods. This is understood to mean radiology methods, advantageously apparatus-based radiology methods, such as for instance computed tomography (CT), x-ray tomography, magnetic resonance tomography (MRT and/or MRI), conventional x-ray, sonography and/or ultrasound examinations, and positron emission tomography.

The landmark data in particular comprises information concerning the geometric differences between the model landmarks which are dependent on the side of the body. These differences which are dependent on the side of the body are in particular differences in the relative position between one or more model landmarks and the position of the reference point; the differences which are dependent on the side of the body can however also be differences in the position of the model landmarks with respect to each other only. The landmark data can also comprise information concerning the position of one model landmark relative to another model landmark, which for example means information concerning the relative distances and/or a geometric pattern which follows from the spatial arrangement of the model landmarks and in particular the reference point. The landmark data advantageously comprises information concerning the differences between such distances and/or relative positions and/or patterns of the model landmarks and in particular the reference point with respect to the arrangement of mutually corresponding model landmarks in different regions of the body, such as for example the differences between the arrangement of the model landmarks and in particular the reference point on a right tibia and fibula and the arrangement of the corresponding model landmarks and in particular the reference point on a left tibia and fibula.

The reference point on the part of the patient's body is advantageously part of the set of patient landmarks; ultimately, both the landmarks and the reference point represent points which are defined and/or referenced, in particular stereotactically, and can thus be recorded in a common data set. The anatomical point data then advantageously includes information concerning the position of the reference point on the part of the patient's body; the landmark data then advantageously also includes information concerning the position of the reference point in the model of the anatomical part of the body. The reference point in the model of the anatomical part of the body is then advantageously part of the set of model landmarks. The reference point then represents an artificial landmark in both the set of patient landmarks and the set of model landmarks.

The position of the reference point is advantageously known and/or defined when an angle α between two straight lines and/or planes, one of which for example comprises a landmark on the lateral malleolus and is perpendicular to the tibial axis and the other of which for example comprises both the landmark on the lateral malleolus and a landmark on the medial malleolus, is small (for example, approximately equal to 0° or 2° or slightly less than 0°, for example −1° or −2°. This can be the case if the position of the landmarks is not established carefully enough during referencing. If, however, the angle a can be clearly determined, i.e. if it for example measures several degrees (for example, 5° or 10° or more), then it is advantageously possible to dispense with establishing the reference point. If, however, the reference point is necessary for a successful lateral determination, a reference star using which its location is established is advantageously aligned anteriorly or posteriorly (i.e. clearly points into one of the half-spaces defined by the frontal plane of the tibia); it is also in particular known whether it is attached medially or laterally to for example the tibia. This then enables the region of the body in the half of the body in which the anatomical part of the body is situated—in particular, the right-hand or left-hand side of the body—to be determined. It is also possible to dispense with establishing the reference point if, as described above, not all the patient landmarks are situated in one plane. A lateral determination can then be made by comparing the characteristic pattern of the positions and/or arrangement of the patient landmarks relative to each other with a position of the model landmarks which is known from a model data set recorded before the beginning of the operation. The lateral determination can then be made by taking into account a characterized position of the at least one patient landmark and model landmark, wherein the characterized position is a position which is not situated in a plane with the positions of the remaining patient landmarks and/or model landmarks.

The anatomical point data and/or landmark data thus also advantageously include information concerning a pattern, in particular a spatial pattern, which is composed not only of the respective positions of the patient landmarks and/or model landmarks relative to each other but in particular also of the relative positions of the patient landmarks and/or model landmarks relative to the reference point (on the part of the patient's body and/or in the model of the anatomical part of the body). A comparison of the anatomical point data and landmark data then for example includes a comparison of the spatial pattern of positions of patient landmarks, model landmarks and in particular at least one reference point, wherein the position of the reference point both on the patient's body and in the model is advantageously taken into account, as applicable. Within the framework of this invention, a "spatial pattern" is in particular understood to mean a distribution of spatial positions, for example a defined multi-dimensional image (advantageously, a three-dimensional or two-dimensional image) of spatial co-ordinates and/or vectors and/or planar co-ordinates and/or vectors (in particular, in a planar projection of said space).

Advantageously, the landmark data is previously known, i.e. regarded as given at the beginning of the method. The landmark data is in particular ascertained with the aid of an imaging method (which the observed part of the patient's body is subjected to).

It is advantageously assumed that the tapped patient landmarks have their counterparts in the set of model landmarks, i.e. advantageously represent the same landmarks. It is in particular assumed that the patient landmarks represent the same landmarks as the model landmarks. This is to be understood to mean that for a patient landmark, a model landmark can be found which exhibits a position in the model of the anatomical part of the body which is comparable and/or similar to the position of the patient landmark in the actual patient's body. In particular, the patient landmarks respectively have positions relative to each other which correspond to the positions of model landmarks relative to each other, such that it is possible on the basis of this to clearly assign the set of patient landmarks to a set of model landmarks. Thus, the set of model landmarks is advantageously obtained from an image of the anatomical part of the patient's body, i.e. in particular does not represent a general set of model landmarks for example for a properly shaped anatomical part of the body which is used for a plurality of patients.

The reference point advantageously also has a counterpart in both the patient data set and the model data set. In particular, the position of the reference point relative to the patient landmarks is comparable to the position of the reference point relative to the model landmarks, i.e. the positional relationships are comparable and/or equivalent to each other. This means that the position of the reference point relative to at least one patient landmark has its geometric counterpart in the position of the reference point relative to at least one model landmark which corresponds to the at least one patient landmark.

The landmark data is advantageously compared with the anatomical point data, such that the region of the body in which the part of the patient's body is situated is determined on the basis of the landmark data and the anatomical point data. It is in particular determined on the basis of the result from the comparison of the landmark data and the anatomical point data. In particular, the positions of the landmarks relative to each other in the patient data set (i.e. the patient landmarks) are compared with the positions of the landmarks relative to each other in the model data set (i.e. the model landmarks). The result of this comparison may be that a particular set of model landmarks, which enables the part of the patient's body to be clearly assigned to a model of the anatomical part of the body, corresponds to the set of patient landmarks. It is then for example possible to ascertain that it is a right tibia and not a left tibia. In this case, the region of the body which is to be determined denotes the right-hand side and/or half of the patient's body and/or the right leg of the patient. Similarly, if it is a left tibia, then the left-hand side and/or half of the patient's body and/or the left leg of the patient is to be determined as the applicable region of the body.

The comparison between the patient landmarks and the model landmarks as described above enables the anatomical part of the body to be assigned to the region of the body without a user having to directly (in particular, manually) assign the positions of patient landmarks to positions of model landmarks. The assignment can rather be made automatically, since the elements of the set of patient landmarks are equal to the elements of the set of model landmarks. In particular, the elements of both sets denote mirror-symmetrical co-ordinates and/or positions of points on the anatomical part of the body and/or in the patient's body, wherein the mirror symmetry preferably exists with respect to a mirror plane and/or symmetry plane in the sagittal plane and/or median sagittal plane of the patient's body and/or the model of the patient's body.

The information concerning the spatial pattern of the positions of the model landmarks describes in particular a positional distribution, i.e. a distribution of the spatial positions of the model landmarks. This space is advantageously described by a patient-centered co-ordinate system, i.e. a co-ordinate system which is defined relative to the patient's body. The positional distribution can thus for example be understood to mean a pattern (in particular, a spatial pattern) and/or a geometric arrangement of the model landmarks in such a co-ordinate system. Such a pattern can then be compared with a pattern which follows from the spatial arrangement of the patient landmarks. The co-ordinate system can be Cartesian and/or spherical. Similarly, the information concerning the spatial pattern of the positions of the patient landmarks can describe a positional distribution of the patient landmarks. The same variants are possible in this case as have just been described for the model landmarks.

It is also possible within the framework of this invention to determine an anterior-posterior direction of the anatomical part of the body. An anterior-posterior direction is in particular understood to mean a direction which runs perpendicular to a frontal plane of the patient's body. If the anatomical part of the body represents a bone in a limb of the patient's body, then the anterior-posterior direction also runs perpendicular to the longitudinal axis of this bone, if the longitudinal axis runs in the proximal-distal direction. The clear assignment of the positional distribution of the patient landmarks to a region of the body, in particular to a right-hand or left-hand side of the body, can also be used—with the aid of other geometric considerations—to determine an anterior-posterior direction of the anatomical part of the body. This directional determination can be important in the surgical navigation method, in order for example to be able to navigate particular instruments relative to the anatomical part of the body.

Correctly determining the region of the body in which the anatomical part of the body is situated is a precondition for this. To this end, it is for example possible to adduce the position of another patient landmark and/or model landmark which is in a characteristic position, in particular a characterized position, relative to one or more other patient landmarks and/or model landmarks, advantageously two other patient landmarks and/or model landmarks. When determining a longitudinal axis and/or anterior-posterior axis of a tibia, for example, it is possible to adduce the patient landmark and/or model landmark on the lateral malleolus in order to clearly assign the referenced patient landmarks to the right-hand or left-hand side of the patient's body and/or to the patient's right or left leg and/or to the equivalent model landmarks in this way. A landmark on the shoulder blade and/or collarbone could also for example be used to assign an upper arm bone to the right-hand or left-hand half of the patient's body. It is also possible in accordance with the invention to use a landmark on the ulna or radius which exhibits a characterized position with respect to other landmarks on the other bone in each case (i.e. either the radius or the ulna), in order to assign the bone which includes the other landmarks to the right or left arm and/or the right-hand or left-hand half of the patient's body. If, for example, the distance between the patient landmark and/or model landmark on the medial malleolus and one of the patient landmarks on the medial condyle and/or lateral condyle and/or intercondylar eminence is compared with the distance between the patient landmark and/or model landmark on the lateral malleolus and at least one of the patient landmarks and/or model landmarks on the medial condyle, lateral condyle or intercondylar eminence and advantageously the known position of a marker device, which in this case is usually attached to the tibia on the medial side of the tubercle of the tibia, then this results in the anatomical part of the body (in this case, the lower leg) being clearly assigned to the right or left leg of the patient. Distances and/or directions between patient landmarks and between the corresponding model landmarks are thus advantageously compared in accordance with the invention.

If the position of the marker device is known, it is also advantageously possible to dispense with determining the distances, and an angular variable between two characteristic straight lines and/or planes can be sufficient for determining the region of the body. Thus, for example, it is possible to place a straight line and/or plane through the positions of the patient landmarks on the medial malleolus and on the lateral malleolus (this straight line advantageously passes through the co-ordinates of at least two patient landmarks) and to draw a perpendicular which is perpendicular to the surface and/or tangent of the surface of the lateral malleolus at the point of the patient landmark on the lateral malleolus. The angle enclosed by the straight line and/or plane and the perpendicular can in particular be used, together with information concerning the position of the reference point, to clearly assign the set of patient landmarks to a right or left tibia.

Alternatively, such a straight line can also be placed through the patient landmark in the lateral malleolus and a patient landmark which is not arranged on the medial malleolus, such as for example the patient landmark in the intercondylar eminence.

Determining distances and/or directions between the patient landmarks and/or model landmarks or determining the angle between the straight line and the perpendicular, as just described, is referred to as determining positional criteria which are dependent on the region of the body to be determined and describe the position of the patient landmarks relative to each other, such that their counterpart in the set of model landmarks can be clearly identified, i.e. the angle and/or the distances and/or directions represent positional criteria.

A longitudinal axis and/or mechanical axis of the part of the body can also be ascertained from the information concerning the region of the body to which the anatomical part of the body is to be assigned. This is in particular possible if the anatomical part of the body represents at least a part of a limb, for example a tibia. If, as described above, the angle between a straight line through two landmarks and a perpendicular onto the surface of a part of the body in which one of the two patient landmarks is situated has been ascertained, then the direction of this perpendicular is known. The landmark in the lateral malleolus advantageously lies on this perpendicular (the perpendicular is therefore referred to in the following as the malleolar perpendicular). A second perpendicular (which is referred to in the following as the longitudinal perpendicular) can then be dropped from the intercondylar eminence onto the malleolar perpendicular, such that the direction of the longitudinal perpendicular coincides with the longitudinal axis of the tibia. The longitudinal axis of the tibia is thus determined.

If, as described above, a malleolar perpendicular (i.e. a perpendicular which runs perpendicular to the longitudinal axis of the part of the body, i.e. a transverse perpendicular) is known, and if the direction of the longitudinal axis of the part of the body is also known, then a third direction can be ascertained which is perpendicular to both the longitudinal axis and the transverse perpendicular. This direction then corresponds to an anterior-posterior direction of the anatomical part of the body. Moreover, the longitudinal axis of the tibia can also determined without determining the transverse perpendicular, if the expected distance between the longitudinal axis and the reference point and/or a known point on a marker device (which is advantageously attached to the reference point) is known. A straight line is thus devised which runs through the landmark on the intercondylar eminence and a virtual point which has a known position relative to the reference point and/or relevant to a point on a marker device. The virtual point advantageously has a known distance from the reference point and/or a known point on the marker device. The direction of the longitudinal axis can thus be devised, with the aid of the known position of the landmark in the intercondylar eminence and the known distance of the reference point and/or a known point on a marker device, as the direction of a straight line through the landmark on the intercondylar eminence and the virtual point.

With the aid of the information concerning the positional distribution of the patient landmarks and as applicable the reference point (and/or a marker device), it is also for example then possible to ascertain whether the user is presented with and/or is observing, from his or her perspective, a front or rear side (an anterior or posterior side) of the body and/or anatomical part of the body (in particular, in the operating environment).

The method in accordance with the invention is advantageously implemented as a data processing method and/or medical data method. The data processing method is preferably performed using technical means, in particular a computer. The computer in particular includes a processor and a memory in order to process the data, in particular electronically. The calculating steps described are in particular performed by a computer. Steps of defining for example ranges or values are in particular steps of establishing data within the framework of the technical data processing method, in particular within the framework of a program. Modifying steps in particular represent modifying the data by means of the computer. Ascertaining steps in particular include retrieving values which are provided at an interface of the computer and have been generated by technical means, such as for example a scanning device. These values are in particular converted by the interface into data which can be processed by the computer.

Within the framework of the invention, computer program elements can be embodied by hardware and/or software (this also comprises firmware, resident software, micro-code, etc.). Within the framework of the invention, computer program elements can take the form of a computer program product which can be embodied by a computer-usable or computer-readable storage medium which includes computer-usable or computer-readable program instructions, "code" or a "computer program" embodied in said medium for use on or in connection with the instruction-executing system. Such a system can be a computer; a computer can be a data processing device comprising means for executing the computer program elements and/or the program in accordance with the invention. Within the context of this invention, a computer-usable or computer-readable medium can be any medium which can comprise, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments. The computer and/or data processing device can in particular comprise a guidance information device which comprises means for outputting guidance information. The guidance information can be output, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The guidance information device advantageously outputs guidance information to a user (in particular, guidance signals) based on the determination of the region of the patient's body. The region of the patient's body which the anatomical part of the body is to be assigned to—such as for example whether it is a right or left tibia—can then be communicated to the user using the visual indicating means and/or the acoustic indicating means (for example, by way of a textual output and/or a speech module output) and/or the tactile indicating means (for example, a vibration means).

A computer-readable medium, on which a program and/or data processing method is stored which performs the method described above when it is loaded onto a data processing device and running on it, is also part of the invention. The data processing device is in particular a commercial computer and/or the computer of a surgical navigation system.

A system for determining the region of the body in which an anatomical part of the body is situated is also part of this invention. Such a system advantageously includes: a pointer for determining the anatomical point data; a computer-readable storage medium on which the landmark data is stored; and a surgical navigation system for comparing the anatomical point data with the landmark data. The surgical navigation system and/or data processing device on which the method in accordance with the invention is running is advantageously configured such that it determines the region of the body in which the part of the patient's body is situated on the basis of the assumption that the patient landmarks represent the same landmarks as the model landmarks and as applicable that the reference point is in a positional relationship with respect to the patient landmarks which is comparable to the positional relationship between the reference point and the model landmarks (providing the reference point is necessary for lateral determination). The region of the body is then advantageously determined on the basis of a comparison of the landmark data and the anatomical point data, as described above.

The system for determining the region of the body can also include the computer-readable storage medium described above and the guidance information device for outputting guidance information, wherein the guidance information advantageously indicates the ascertained region of the body to which the anatomical part of the body has been assigned.

DETAILED DESCRIPTION

The reference sign X is used in the following as an abbreviation for the set of reference signs 1a, 3, 4, 5, 6, 7. The reference sign Y is used in the following as an abbreviation for the set of reference signs 17, 18, 20, 21, 22, 23.

Figure 1:
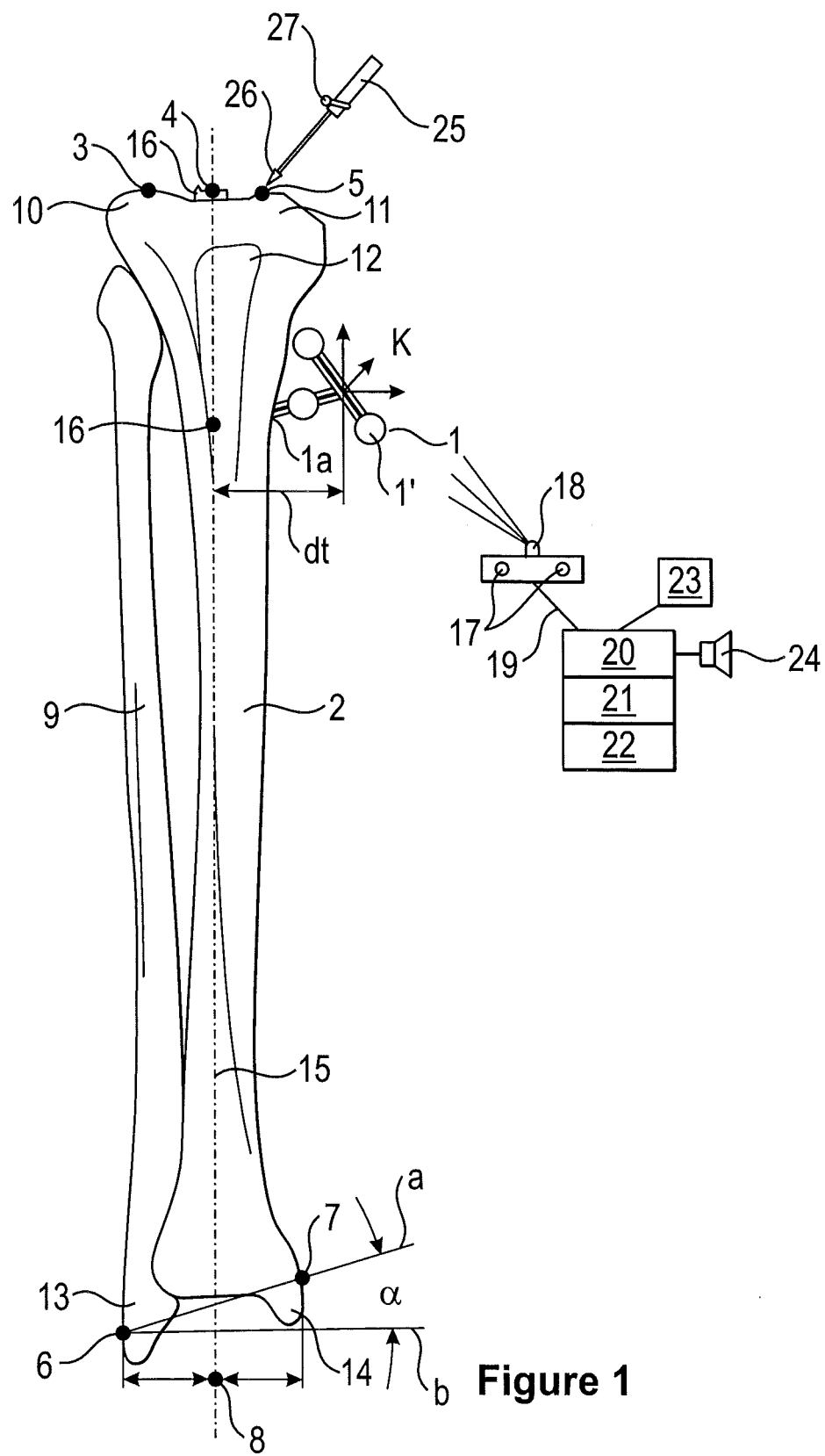
FIG. 1 shows a tibia and a fibula, together with a marker device and a surgical navigation system.

FIG. 1 shows the position of the patient landmarks X on a tibia and a fibula, and the tibial axis (longitudinal axis) being ascertained with the aid of a surgical navigation system. A reference star 1 is attached on a tibia 2 in the reference point 1a in the region of the tubercle 12 of the tibia. It is also possible to dispense with the reference star 1 if the reference point 1a is registered and/or established with the aid of a pointer 25 at the beginning of the method or if at least one patient landmark X does not lie in a common plane with the other patient landmarks X. Registering comprises assigning the reference point 1a in the patient data set to the corresponding co-ordinates in the model data set. The surgeon can tap the patient landmarks X with the aid of the pointer 25 which includes marker spheres 27 and a tip 26 of the pointer. The user thus enables a surgical navigation system Y to detect the co-ordinates and/or positions of the patient landmarks X relative to a co-ordinate system K. The co-ordinate system K can be fixed with respect to the patient's body and/or the anatomical part of the body (for example, the tibia 2). The co-ordinate system K can however also be fixed with respect to an origin which is situated outside the patient's body, for example at the location of the surgical navigation system Y.

The surgical navigation system Y includes a transmitter 18 for infrared radiation and two receivers (in particular, a stereotactic camera) 17 which are sensitive to infrared radiation. A data line 19 communicates signals between a processor 20 and the transmitter 18 and receiver 17. A monitor 23 and a guidance information device 24 for outputting audible and/or visible guidance information to a user are also connected to the processor 20. The guidance information device 24 advantageously includes a loudspeaker and can be integrated into the monitor 23. A working memory 21 and a permanent memory 22 (for example, a hard disc or other magnetic and/or optical computer-readable storage medium) are also connected to the processor 20. The landmark data and the positional criteria (a) can be stored in the permanent memory 22.

The user can then tap patient landmarks X using the pointer 25. Said landmarks are advantageously arranged as follows: one landmark 3 is situated on the lateral condyle 10, one landmark 4 is situated on the intercondylar eminence 16, one landmark 5 is situated on the medial condyle 11, one landmark 6 is situated on the lateral malleolus 13, and one landmark 7 is situated on the medial malleolus 14. It will therefore be clear that a landmark (namely the landmark 6) is also arranged on the fibula 9. The surgical navigation system Y then imports the anatomical point data, from which it ascertains a positional distribution of the positions of patient landmarks X. The position of the reference point 1a and/or the reference star 1 relative to the tibia 2 can also be known to the surgical navigation system Y. The reference point 1a and/or the point at which the reference star 1 is affixed advantageously lies in the region of the tubercle 12 of the tibia. Since the reference point 1a can be tapped using the pointer 25 even without using the reference star 1, the position of the reference point 1a relative to the tibia 2 is known to the surgical navigation system Y whether the reference star 1 is used or not.

Figure 1A:
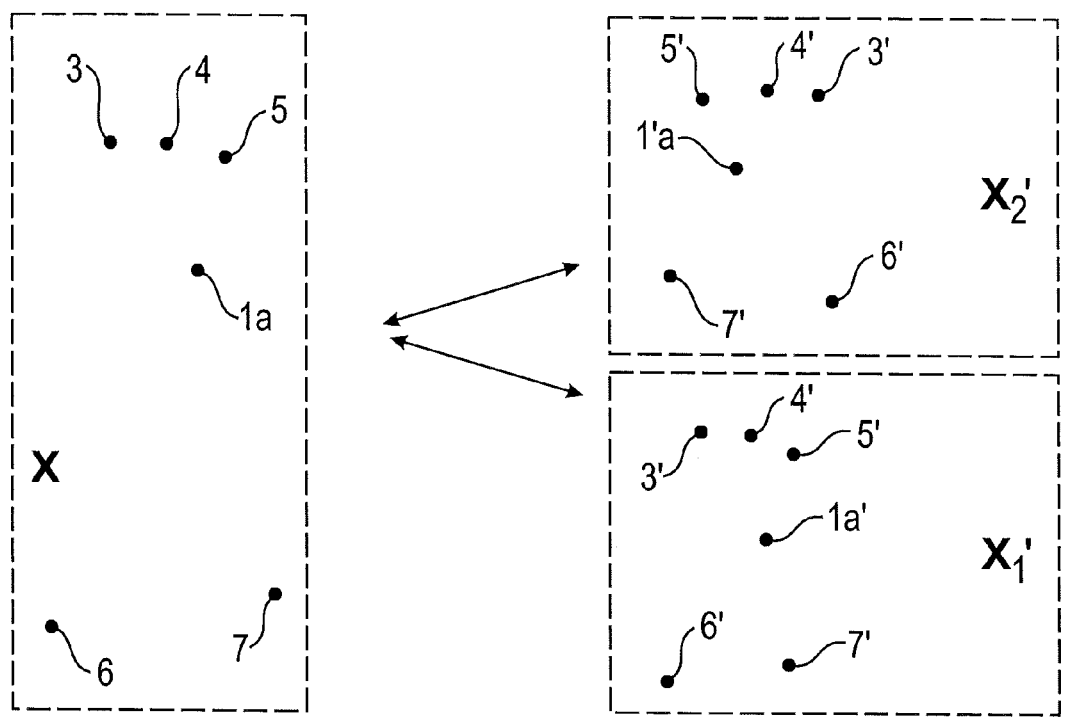
FIG. 1a schematically shows the positional distribution of the patient landmarks being compared with the positional distributions of two sets of model landmarks which are axially symmetrical to each other.

FIG. 1a plots a comparison between the set of patient landmarks X and two sets of model landmarks $X_1'$, $X_2'$, wherein each set consists of model landmarks which correspond to the model of the anatomical part of the body on a particular side of the body, wherein the set $X_1'$ includes model landmarks 3', 4', 5', 6', 7' and a reference point 1a' (which can also be regarded as a model landmark), wherein a set $X_2'$ includes the corresponding model landmarks for the part of the body which in the model is mirror-symmetrical to the set of model landmarks $X_1'$ with respect to a sagittal plane (in particular, the median sagittal plane) of the model of the patient's body. If, for example, the set of patient landmarks X with respect to the reference point 1a represents the geometric relationships on a right lower leg of the patient, then a comparison with the sets of model landmarks $X_1'$ and $X_2'$ (the position of which relative to reference points 1a' is defined) reveals that the arrangement of the patient landmarks X corresponds to the arrangement of the model landmarks $X_1'$ with a greater degree of probability than to the arrangement of the model landmarks $X_2'$.

Figure 1B:
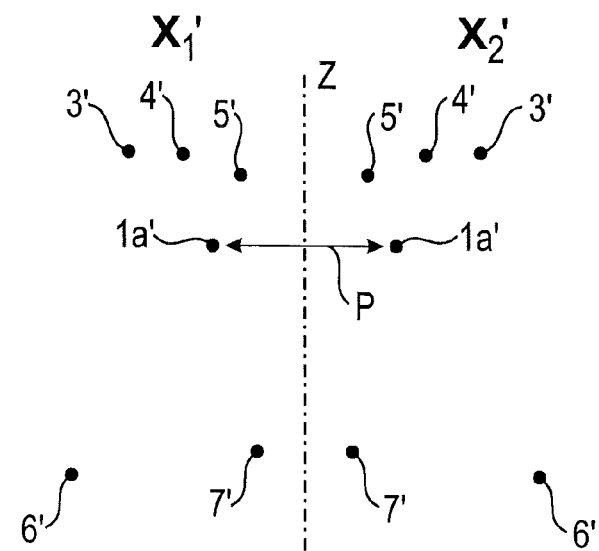
FIG. 1b shows the symmetry relationships between two sets of model landmarks on different sides.

This becomes all the clearer when considering FIG. 1b, which shows the symmetry relationships between the sets of model landmarks $X_1'$ and $X_2'$ with respect to an axis z which lies in the median sagittal plane of the patient. If the patient landmarks X are then tapped in the order in which they are numbered, this results in a characteristic distribution of the patient landmarks X in particular with respect to the position of the reference point 1a. This distribution in particular comprises information concerning the distances between the patient landmarks X and advantageously information concerning angles (preferably, planar and/or spatial angles) between straight lines which connect the individual patient landmarks X to each other. The same information exists concerning the sets of model landmarks $X_1'$ and $X_2'$. Information on the order in which the positions of the model landmarks relative to the reference point $1a'$ are to be compared with the positions of the patient landmarks X relative to the reference point $1a$ can also exist for each of the sets of model landmarks $X_1'$ and $X_2'$. It follows from FIG. 1$b$ that the positions of the model landmarks relative to the reference point $1a'$ are different with respect to a symmetry axis z in the sagittal plane of the model of the patient's body. By comparing with the positions of the patient landmarks X relative to the reference point $1a$, it is possible to ascertain—on the basis of said difference—the set of model landmarks $X_1'$, $X_2'$ which the set of patient landmarks X matches. Within this context, a "match" refers in particular to a geometric similarity between the positional distributions of the set of patient landmarks X and the sets of model landmarks $X_1'$ and $X_2'$. This similarity is based on the comparison of distances and/or angles and/or directions as described above. The method in accordance with the invention does however advantageously permit deviations between the positional distributions in the set of patient landmarks X and the applicable set of model landmarks $X_1'$, $X_2'$ (i.e. the set of model landmarks which is in particular geometrically similar to the set of patient landmarks X), such that a match can be established even if this deviation exists. Such a deviation can in particular be a relative error between the locations of the landmarks which for example has a value of $10^{-2}$ or also $10^{-3}$ and/or which lies within an interval which has an upper limit of $10^{-1}$ or $10^{-2}$ or $10^{-3}$ and a lower limit of $10^{-2}$ or $10^{-3}$ or $10^4$. It is also possible in accordance with the invention to define an absolute deviation which can for example measure 1 μm, 1 mm or 5 mm or can lie within an interval which advantageously has an upper limit of 5 mm or 1 mm and advantageously has a lower limit of 1 mm or 1 μm. In FIG. 1 b, the double-headed arrow P also clearly shows the axially symmetrical position of the reference points $1a'$ with respect to a symmetry axis z of for example the right (model landmarks $X_1'$) and left (model landmarks $X_2'$) lower extremity of a model of the patient's body. The reference point $1a'$ is in particular arranged at mutually corresponding points on the two symmetrical parts of the body (i.e. points which are respectively in the same position relative to the tubercle 12 of the tibia).

The surgical navigation system Y can calculate the position of a straight line a through the patient landmarks 7 and 6 and the position of a perpendicular b onto a tangential plane through the surface of the lateral malleolus 13 in the point of the patient landmark 6, from which the surgical navigation system Y in turn ascertains the value of the angle α enclosed by the straight line a and the transverse perpendicular b. This angle α is then compared with a previously known value of this angle for the positional distribution of the landmarks X. When for example the result is that the landmark 6 is situated further away from the reference point $1a$ than the landmark 7, it can be assumed that this is a left lower leg: the patient landmarks X are preferably tapped in the order in which they are numbered by the reference signs and/or in an order which is established beforehand, in particular beginning at the reference point $1a$, such that the position of the patient landmark 6 relative for example to the reference point $1a$ and to the patient landmark 7 is characteristic of the right-hand or left-hand side of the patient's body.

The surgical navigation system Y (and/or its processor 20) can also for example calculate a straight line 15 which is both perpendicular to the transverse perpendicular b and passes through the patient landmark 4 on the intercondylar eminence 16. The straight line 15 thus in particular coincides with the longitudinal axis of the tibia and/or a central tibial axis in the longitudinal direction of the tibia, wherein the longitudinal axis advantageously runs from the intercondylar eminence towards the distal end of the tibia. It is also known that this straight line divides the projection of the straight line a onto the transverse perpendicular b exactly into two parts of equal size. The distance between a point 8 and a tangent onto the surface of the medial malleolus at the point of the patient landmark 7 is equal to the distance between the point 8 and a tangent onto the surface of the lateral malleolus at the point of the patient landmark 6; the point 8 can thus be regarded as the mid-point of the distance between the landmarks 6 and 7. Using this information, it is possible to devise and/or calculate the position of the tibial axis 15 and/or the longitudinal axis 15 of the tibia by placing a straight line 15 through the point 8 and the landmark 4. It can also be known that the tibial axis 15 is to have a particular distance dt from a component of the reference star and is to be parallel to an axis of the co-ordinate system K, for example in a point $1b$ which advantageously lies between the point 8 and the landmark 4, wherein the relevant axis of the co-ordinate system K preferably runs parallel to the sagittal plane of the patient's body and/or the model of it. The tibial axis 15 can also be devised from these two items of information which describe the position of the tibial axis 15 relative to the reference star 1.

Figure 2:
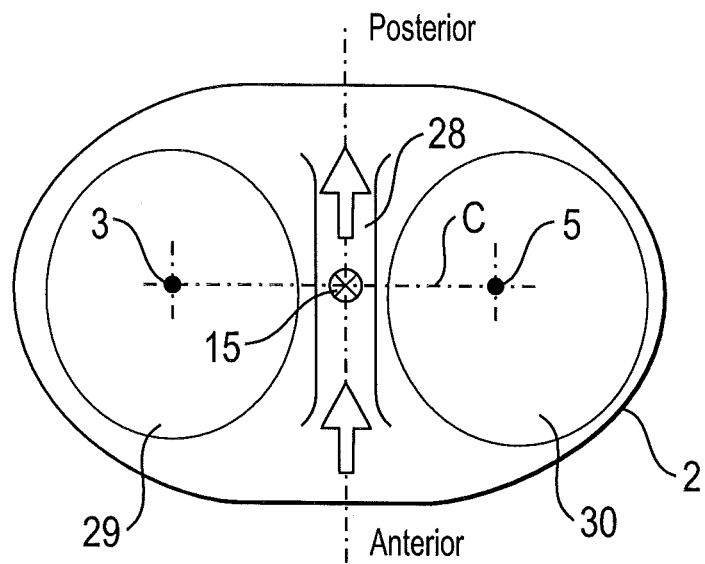
FIG. 2 shows an axial view of a tibia, with an anterior-posterior direction marked.
Figure 3:
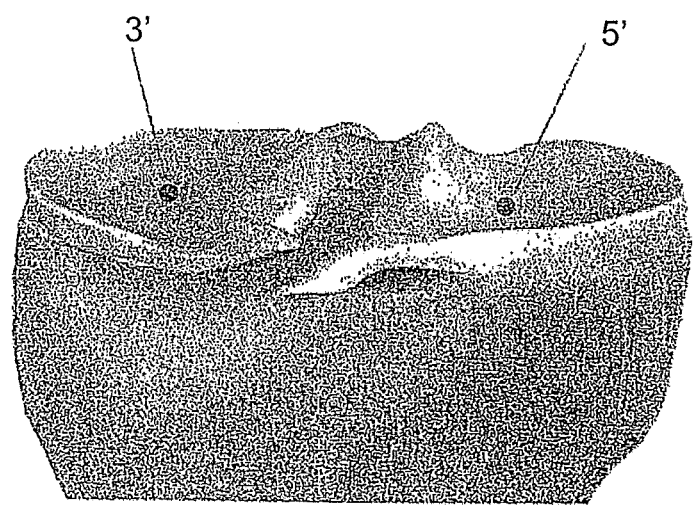
FIG. 3 shows the landmarks in the medial condyle and lateral condyle.

FIG. 2 shows the relationship of an anterior-posterior direction 28 of the tibia 2 to the direction of the transverse perpendicular b and the direction of the tibial axis 15. The transverse perpendicular b runs parallel to a straight line through the two patient landmarks 3 and 5 which lie in the lateral plateau 29 and the medial plateau 30 of the tibia 2 shown. The tibia 2 represents in particular a right tibia in an anterior view. FIG. 3 illustrates the three-dimensional position of the patient landmarks 3 and 5 in the form of the model landmarks 3' and 5' on the condyles.

Since the straight line c runs perpendicular to the direction of the tibial axis 15 and preferably parallel to the transverse perpendicular b, the surgical navigation system Y (and/or its processor 20) can calculate a plane which is perpendicular to both directions, and in which the anterior-posterior direction 28 lies, from the knowledge of the direction of the transverse perpendicular b and tibial axis 15. It is thus also possible to output to the user, by means of the guidance information device 24, guidance information as to whether the user is currently using an instrument, provided with a marker device, on the anterior or posterior side of the tibia 2.

Figure 4:
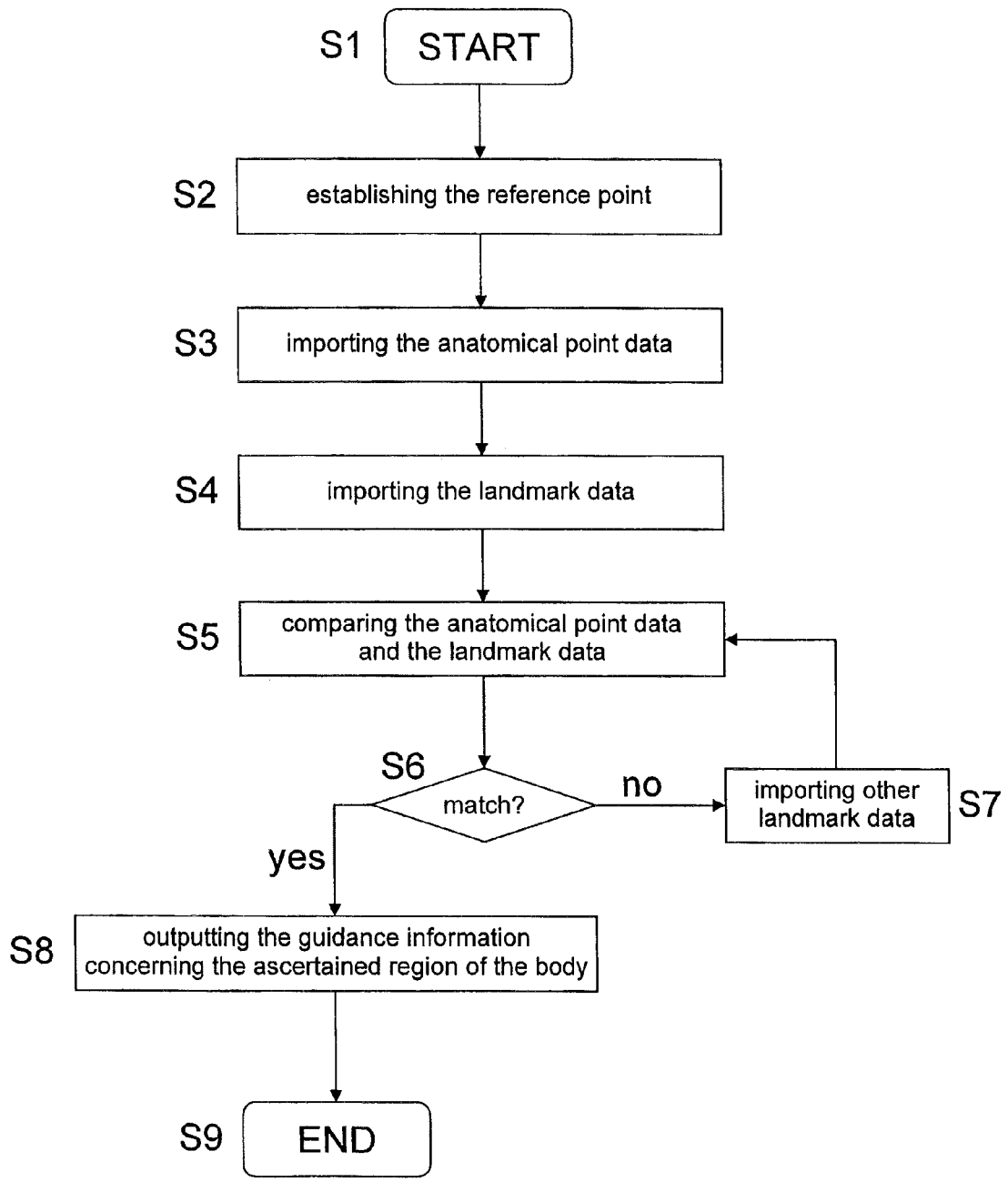
FIG. 4 shows a flow diagram of the method in accordance with the invention.

FIG. 4 shows a flow diagram for the method in accordance with the invention, which efficiently embodies the comparison between the anatomical point data and the landmark data. The method is intended to be performed on a data processing device 20, 21, 22 and therefore has the structure of a data processing program. The program starts by being retrieved by the processor 20 in a step 51. The reference point is advantageously established in a step S2 by the surgical navigation system ascertaining the position of the reference point $1a$ as a result of tapping it using a pointer 25 or from the detected position of a reference star 1. If a reference star 1 is used, the position which the reference point $1a$ exhibits relative to the markers 1' of the reference star 1 is known. In a step S3, the surgical navigation system Y imports the anatomical point data and therefore the positions of the patient landmarks X, in particular relative to the reference point $1a$, advantageously with the aid of tapping them using a pointer 25. In a step S4, the processor 20 imports the landmark data, advantageously from the permanent memory 22. In particular, the user can choose the anatomical part of the body 2, 9 which is intended to be treated within the framework of the method, before the beginning of the method. It is thus possible to adapt the program to initially import only a set of model landmarks which corresponds to the arrangement of the anatomical part of the body 2, 9 in a particular region of the body (for example, on the left-hand side of the body) which has been communicated to the program. This avoids importing landmark data which relates to landmarks lying in a region of the body other than the region of the body being observed. In a step S5, a positional distribution of the patient landmarks X (and/or anatomical point data) is then compared with a positional distribution $X_1'$, $X_2'$ of the model landmarks $1'a$, $3'$, $4'$, $5'$, $6'$, $7'$ (and/or the landmark data), and in a step S6, the result of this comparison is evaluated with respect to a match between the data sets. Within this context, a match between the data sets means that the positional distribution of the patient landmarks X corresponds to the positional distribution $X_1'$, $X_2'$ of the model landmarks $1'a$, $3'$, $4'$, $5'$, $6'$, $7'$ which were imported in step S4 in the form of the landmark data. This correspondence can be ascertained using the criteria described above for the match between the positional distribution in a set of patient landmarks X and the positional distribution in a set of model landmarks $X_1'$, $X_2'$. If there is a match, guidance information can be output to the user in a step S8 which informs the user as to the region of the body which the anatomical part of the body 2, 9 is to be assigned to. This guidance information can for example be output as audio information via the guidance information device 24; it is however also possible in accordance with the invention to output graphic information (for example by highlighting the ascertained region of the body in color in a graphic representation of the human body on the monitor 23) or in the form of a textual output on the monitor 23. If, however, step S6 does not reveal a match, then the second set of model landmarks $1'a$, $3'$, $4'$, $5'$, $6'$, $7'$ which is applicable in principle (i.e. on the basis of an operation plan) due to its symmetry is not imported until a step S7 and is fed to a comparison with the anatomical point data in step S5. This avoids importing data which will certainly not lead to the desired result of a match in S6. It is, however, also possible to dispense with step S7 and deduce, from the lack of a match in step S6, that the part of the body 2, 9 is to be assigned to another particular region of the body. This approach is justified in the case of a tibia 2, for if the positional distribution of the patient landmarks X does not for example generate a match in step S6 when compared with model landmarks $1'a$, $3'$, $4'$, $5'$, $6'$, $7'$ of a left tibia of the patient in step S5, then the tibia 2 must necessarily represent the right tibia of the patient. In this way, it is also possible to avoid using an imaging method to provide patient data of the second anatomical part of the body which is advantageously symmetrical (in particular, mirror-symmetrical with respect to the median sagittal plane of the patient's body and/or the model of the patient's body) and respectively inapplicable to the operation. If, however, step S7 is incorporated into the method in accordance with the invention, then a positive test concerning the match between the positional distribution of patient landmarks X and the positional distribution $X_1'$, $X_2'$ of model landmarks $1'a$, $3'$, $4'$, $5'$, $6'$, $7'$ can be performed in step S5. This provides the user with a confirmation that his/her approach is correct. The program ends in a step S9, and the information concerning the match from step S6 and the applicable region of the body can be stored in the permanent memory 22 or in the working memory 21 by the processor 20 and used for the subsequent surgical navigation method.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

LIST OF REFERENCE SIGNS 1 reference star
1a reference point on the part of the patient's body 2, 9
1a' reference point in the model of the anatomical part of the body
2 tibia
3 patient landmark on the lateral condyle 10
3' model landmark on the lateral condyle 10
4 patient landmark on the intercondylar eminence 16
4' model landmark on the intercondylar eminence 16
5 patient landmark on the medial condyle 11
5' model landmark on the medial condyle 11
6 patient landmark on the lateral malleolus 13
6' model landmark on the lateral malleolus 13
7 patient landmark on the medial malleolus 14
7' model landmark on the medial malleolus 14
8 distance between the landmarks 6, 7 on the lateral malleolus 13 and medial malleolus 14 and the tibial axis 15
9 fibula
10 lateral condyle
11 medial condyle
12 tubercle of the tibia
13 lateral malleolus
14 medial malleolus 15 tibial axis
16 intercondylar eminence
17 receiver
18 transmitter
19 data line
20 processor
21 working memory
22 permanent memory
23 monitor
24 guidance information device
25 pointer
26 tip of the pointer
27 pointer marker
28 anterior-posterior direction
29 lateral plateau
30 medial plateau
S1 program start
S2 establishing the reference point
S3 importing the anatomical point data
S4 importing the landmark data
S5 comparison
S6 checking for a match
S7 importing other landmark data
S8 guidance information
S9 program end

What is claimed is:

1. A non-transitory computer readable medium including a program for determining a region of the body in which an anatomical part of the body is situated, said program being configured to cause a computer on which the program is executed to:
   obtain anatomical point data which includes information concerning a spatial pattern of positions of patient landmarks of a part of a patient's body which corresponds to the anatomical part of the body;
   obtain landmark data which includes information concerning a spatial pattern of positions of model landmarks of a model of the anatomical part of the patient's body;
   determine, based on the landmark data and the anatomical point data and an assumption that the patient landmarks represent the same landmarks as the model landmarks, the region of the body in which the part of the patient's body is situated, wherein the patient landmarks include an artificial landmark on the part of the patient's body and anatomical landmarks on the part of the patient's body, and the model landmarks include an artificial landmark in the model and anatomical landmarks in the model;
   wherein the position of the artificial landmark on the part of the patient's body corresponds
   to the position of a marker device on the part of the patient's body.

2. The program according to claim 1, wherein the anatomical point data is provided in such a way that the positions of patient landmarks are not directly assigned to positions of model landmarks, wherein elements of a set of patient landmarks are equal to elements of a set of model landmarks.

3. The program according to claim 1, wherein the information concerning the spatial pattern of the positions of the model landmarks describes a positional distribution of the model landmarks, and the information concerning the spatial pattern of the positions of the patient landmarks describes a positional distribution of the patient landmarks.

4. The program according to claim 1, wherein positional criteria are provided which describe criteria, which are dependent on the region of the body, for the position of the patient landmarks with respect to each other and/or for the position of the model landmarks with respect to each other.

5. The program according to claim 1, wherein determining the region of the body includes determining an angle between a straight line through at least two particular patient landmarks and/or model landmarks and a perpendicular with respect to a surface section of the part of the patient's body, wherein the position of one of the particular patient landmarks and/or model landmarks includes the surface section.

6. The program according to claim 1, wherein determining the region of the body includes determining the region of the body to be a left-hand or right-hand side of the body.

7. The program according to claim 1, further comprising determining information concerning an anterior-posterior direction of the part of the patient's body.

8. The program according to claim 1, wherein determining the region of the body includes determining the region of the body to be an anterior or posterior side of the body.

9. The program according to claim 1, further comprising determining information concerning the position of a tibial axis.

10. The program according to claim 1, further comprising outputting guidance information to a user on the basis of determining the region of the patient's body.

11. A navigation system for determining the region of the body in which an anatomical part of the body is situated, said navigation system including:
    a pointer for determining anatomical point data which includes information concerning a spatial pattern of positions of patient landmarks of a part of a patient's body which corresponds to the anatomical part of the body;
    a computer-readable storage medium on which landmark data is stored which includes information concerning a spatial pattern of positions of model landmarks of a model of the anatomical part of the patient's body;
    a surgical navigation system for comparing the anatomical point data with the landmark data,
    a computer-readable medium on which the program according to claim 1 is stored,
    wherein the surgical navigation system includes a data processing device which is configured to perform the program according to claim 1.

12. The system according to claim 11, which comprises a guidance information device for outputting guidance information which is based on the comparison between the landmark data and the anatomical point data.

* * * * *